(12) United States Patent
Robotti et al.

(10) Patent No.: US 7,425,451 B2
(45) Date of Patent: Sep. 16, 2008

(54) TRIAZINE DERIVATIVES AS UNIVERSAL PEPTIDE ISOTOPE TAG REAGENTS (U-PIT)

(75) Inventors: Karla M. Robotti, Mountain View, CA (US); James Alexander Apffel, Jr., Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 601 days.

(21) Appl. No.: 10/318,845

(22) Filed: Dec. 13, 2002

(65) Prior Publication Data

US 2004/0115821 A1 Jun. 17, 2004

(51) Int. Cl.
- G01N 33/00 (2006.01)
- C07D 403/00 (2006.01)
- A01N 43/66 (2006.01)
- A61K 31/53 (2006.01)

(52) U.S. Cl. ............ 436/86; 544/209; 514/245
(58) Field of Classification Search ........... 436/86; 514/245; 544/209
See application file for complete search history.

(56) References Cited

U.S. PATENT DOCUMENTS

| | | | |
|---|---|---|---|
| 6,271,037 | B1 | 8/2001 | Chait et al. |
| 6,312,893 | B1 | 11/2001 | Van Ness et al. |
| 6,379,971 | B1 | 4/2002 | Schneider et al. |
| 2002/0037532 | A1 | 3/2002 | Regnier et al. |

| 2002/0076817 | A1 | 6/2002 | Figeys et al. |

FOREIGN PATENT DOCUMENTS

| WO | WO 00/11208 | 3/2002 |
|---|---|---|
| WO | WO 02/29414 A2 | 4/2002 |
| WO | WO 02/42427 A2 | 5/2002 |

OTHER PUBLICATIONS

Yamada et al., "An S-Alkylatinf Reagent With Positive Charges As An Efficient Solubilizer Of Denatured Disulfide-Containing Proteines", Journal Of Biochemistry, Japanese Biochemical Society, Tokyo, JP, vol. 116, 1994, pp. 852-857.

Janda et al., "Antibody Bait and Switch Catalysis: A Survey Of Antigens Capable Of Inducing Abzymes WithAcyl-Transfer Properties", Journal Of The American Chemical Society, vol. 113, No. 14, 1991, pp. 5427-5434.

Lu et al., "Water Soluble Dialkyl Peroxides And Peroxyesters", Journal Of Organic Chemistry, AmericanChemical Society. Easton, US, vol. 60, No. 16, Aug. 11, 1995. pp. 5341-5345.

(Continued)

*Primary Examiner*—Jill Warden
*Assistant Examiner*—Keri A Moss

(57) ABSTRACT

Compounds, compositions, methods for sequencing proteins and peptides, and methods for identifying proteins and peptides in a mixture, are disclosed. Compounds of formula A-B-C wherein A is a nucleophilic reactive group, B is a detectable moiety capable of being isotopically labeled, and C is a charge replacement group, are used to label the peptides at the N-terminus or the C-terminus. The tagged peptides can then be analyzed by mass spectroscopy.

27 Claims, 4 Drawing Sheets

OTHER PUBLICATIONS

Calvani et al, "L-Carnitine Esters AS "Soft", Broad-Spectrum Antimicrobial Amphipiles", Journal Of Medicinal Chemistry, American Chemical ISociety. Washington, US, vol. 41, No. 13, 1998, pp. 2227-2233.

Brancia et al., "Investigation Of The Electrospray Response Of Lysinearginine-, And Homoarginine-Terminal Pepetide Mixtures By Liquid Chromatography/Mass Spectrometry", Rapid Communication In Mass Spectrometry, Hyden, London, GB, vol. 16, No. 24, 2002, pp. 2255-2259.

Bull et al., "Development Of An Immunoassay For A Quaternary Ammonium Compound, Benzyldimethyldodeclammonium Chloride", Water Research, Elsevier Science Publishers, Amsterdam, NL, vol. 32, No. 12, Dec. 01, 1998, pp. 3621-3630.

Ducret et al., *Protein Science* 7:706-719 (1998).

Goshe et al, "Phosphoprotein Isotope-Coded Affinity Tags: Application to the Enrichment and identification of Low-Abundance Phosphoproteins," *Anal. Chem.* 74:607-616 (2002.

Goshe et al., "Phosphoprotein Isotope-Coded Affinity Tag Approach for Isolating and Quantitating Phosphopeptides in Proteome-Wide Analyses," *Anal. Chem.* 73:2578-2586 (2001).

Gygi et al., "Quantitative Analysis of Complex Protein Mixtures Using Isotope-Coded Affinity Tags," *Nature Biotechnology* 17:994-997 (1999).

Munchbach et al., "Quantitation and Facilitated de Novo Sequencing of Proteins by Isotopic N-Terminal Labeling of Peptides with a Fragmentation-Directing Moiety," *Anal. Chem* 72:4047-4157 (2000).

Yao et al., *Anal. Chem.* 73:2836-2842 (2001).

TRIAZINE DERIVATIVES AS UNIVERSAL PEPTIDE ISOTOPE TAG REAGENTS (U-PIT)

TECHNICAL FIELD

The present invention pertains generally to proteins and peptides. In particular, the invention relates to compounds, compositions and methods for determining the identity and sequence of proteins and peptides, and the differential expression of proteins.

BACKGROUND OF THE INVENTION

Protein sequencing has traditionally been carried out using Edman degradation. However, the technique is slow and can require significant amounts of the protein. In order to overcome the disadvantages of Edman degradation, several new techniques have been developed. One technique is based on the separation of complex protein samples by two-dimensional gel electrophoresis and the subsequent sequential identification of the separated protein species (Ducret et al. (1998) Protein Sci. 7: 706-719). In a further refinement, the separated proteins are analyzed by mass spectrometric techniques and the protein and peptide mass spectral data correlated with sequence databases, thereby allowing for the rapid identification of proteins and peptides. However, the technique is sequential in nature, thereby limiting the number of samples that can be processed. Moreover, the method is difficult to automate.

In another method, called Isotope Coded Affinity Tags (ICAT), the protein-containing sample is derivatized with a cysteine specific reagent which contains a heavy/light form. After tagging, the samples are pooled, digested and the tagged fragments separated by affinity chromatography. The isolated fragments are subsequently analyzed by LC-MS or MALDI-TOFMS (WO 00/11208 to Aebersold et al.). The method thus assumes that every peptide or protein contains a cysteine that can be derivatized and that protein identity can be ascertained from the thiol-containing peptide fragment. In a related technique, termed Phosphoprotein Isotope Coded Affinity Tag (PhIAT), the O-phosphorylation sites of serine, threonine and tyrosine are isotopically enriched, the proteins separated and analyzed by mass spectroscopy (Goshe et al. (2001) Anal. Chem. 73: 2578-2586). The PhIAT methodology does not appear to work with tyrosyl phophorylation, and the methodology is additionally limited to a single application of phosphorylation.

In another approach, the peptide is proteolytically digested in $^{18}$O-enriched water whereby the carboxyl terminus of each peptide is isotopically labeled (Yao et al. (2001) Anal. Chem. 73: 2836-2842, U.S. Patent Publication No. 2002/0076817 to Figeys et al.). The isotopically labeled peptides are quantitated by comparison with a control sample digested in normal water where the mass spectrometer of the labeled peptide is shifted by 4 amu over the control. However, due to the small mass difference between the labeled peptide and the control, there are interferences with natural isotope distribution and resolution of the multiply charged peptides.

There remains a need, therefore, for compositions and methods for assaying and sequencing proteins and peptides.

SUMMARY OF THE INVENTION

The present invention provides compounds of formula:

A-B-C wherein:
A is a nucleophilic reactive group; B is a detectable moiety capable of being isotopically labeled; and C is a charge replacement group. In some of the compounds of the invention, A comprises:

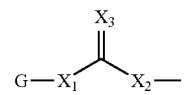

wherein
G is selected from the group consisting of succinimide, maleimidie, glutarimide, isatin, phthalimide and halo-acetone; $X_1$ and $X_3$ are independently selected from the group consisting of $CR_1R_2$, S, and $NR_3$ wherein $R_1$, $R_2$, $R_3$ are independently hydrogen or lower alkyl; and $X_2$ is a direct bond or is selected from the group consisting of $CR_1R_2$, S, and $NR_3$ wherein $R_1$, $R_2$, $R_3$ are independently hydrogen or lower alkyl.

Also provided are compounds of formula:

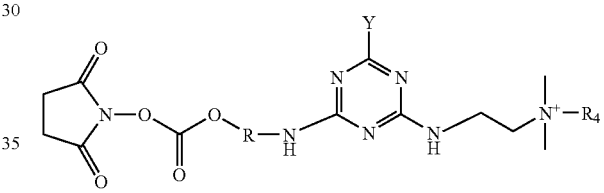

where Y is H, halogen, or of the formula: —X'—R'; where X' is NH, O, or S; R' is selected from the group consisting of hydrogen, alkyl, alkenyl, alkynyl, aryl, and heteroaryl; R is selected from the group consisting of alkyl, alkenyl, alkynyl, aryl, heteroaryl, and $(CH_2CH_2O)_n$ where n is an integer between 1 and 5; and $R_4$ is selected from the group consisting of hydrogen, lower alkyl and aryl. In some of the compounds, X', R' and/or R are isotopically labeled.

The invention also provides compounds of the formula:

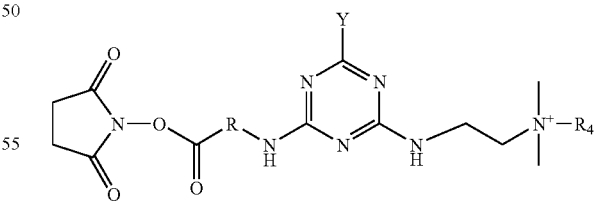

where Y is H, halogen, or of the formula: —X'—R'; where X' is NH, O, or S; R' is selected from the group consisting of hydrogen, alkyl, alkenyl, alkynyl, aryl, and heteroaryl; R is selected from the group consisting of alkyl, alkenyl, alkynyl, aryl, heteroaryl, and $(CH_2CH_2O)_n$ where n is an integer between 1 and 5; and $R_4$ is selected from the group consisting of hydrogen, lower alkyl and aryl. In some of the compounds, X', R' and/or R are isotopically labeled.

The invention also provides kit for detecting the presence of a plurality of target peptides in a sample, the kit comprising a compound of formula A-B-C wherein A is a nucleophilic reactive group, B is a detectable moiety capable of being isotopically labeled, and C is a charge replacement group; and written instructions. The kits can include compounds of formula:

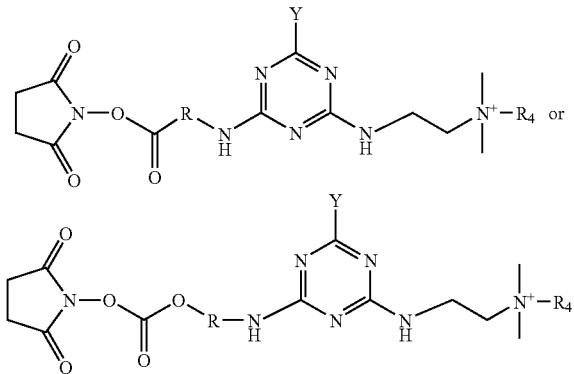

where Y is H, halogen, or of the formula: —X'—R'; where X' is NH, O, or S; R' is selected from the group consisting of hydrogen, alkyl, alkenyl, alkynyl, aryl, and heteroaryl; R is selected from the group consisting of alkyl, alkenyl, alkynyl, aryl, heteroaryl, and $(CH_2CH_2O)_n$ where n is an integer between 1 and 5; and $R_4$ is selected from the group consisting of hydrogen, lower alkyl and aryl.

These and other aspects of the present invention will become evident upon reference to the following detailed description and attached drawings. In addition, various references are set forth herein which describe in more detail certain procedures or compositions, and are therefore incorporated by reference in their entireties.

DETAILED DESCRIPTION OF THE INVENTION

Figure 1:
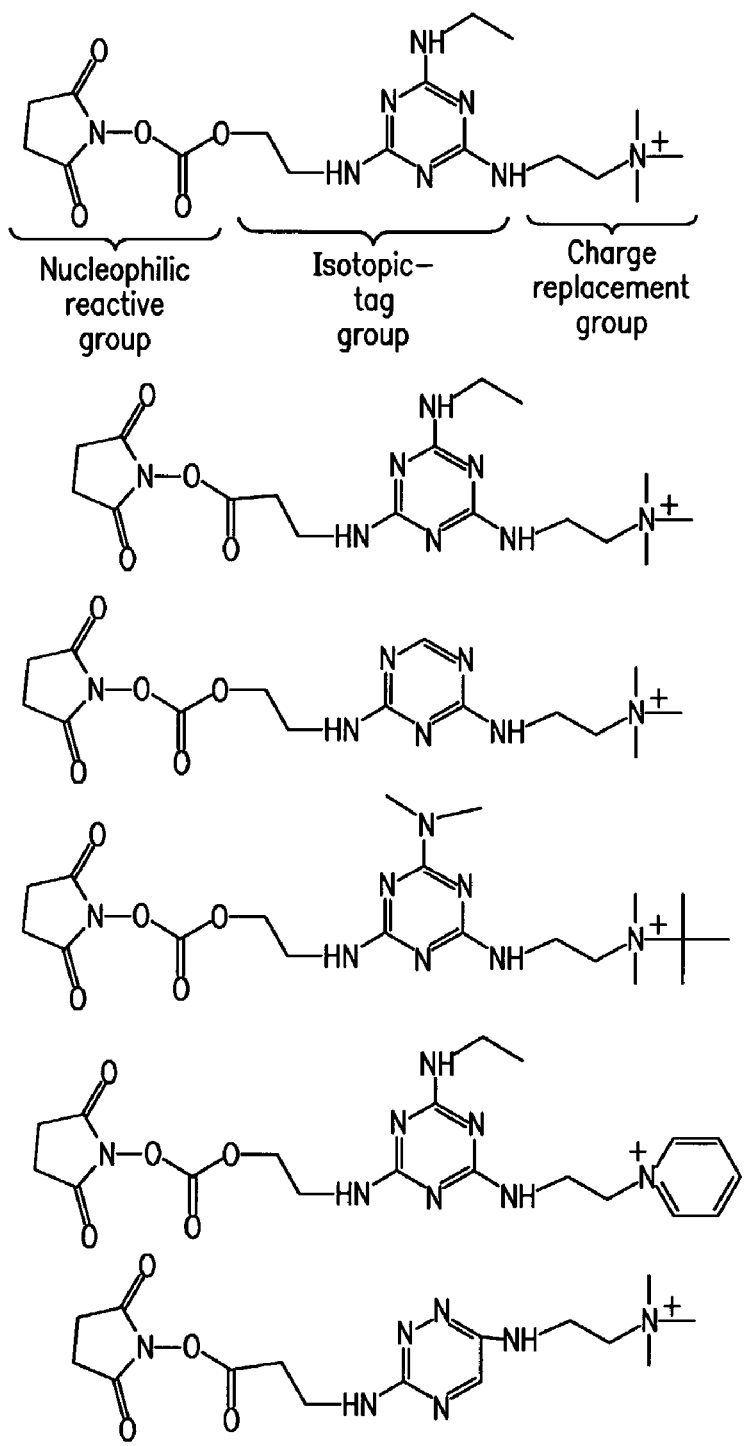
FIG. 1 depicts exemplary U-PIT reagents.

Unless otherwise defined below, the terms used herein have their normally accepted scientific meanings. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. Such techniques are explained fully in the literature. See, for example, G. Barany and R. B. Merrifield (1980) "The Peptides: Analysis, Synthesis, Biology" Vol. 2, E. Gross and J. Meienhoffer, eds. Academic Press, New York., *Methods In Enzymology* (S. Colowick and N. Kaplan eds., Academic Press, Inc.); *Remington's Pharmaceutical Sciences*, 18th Edition (Easton, Pa.: Mack Publishing Company, 1990); F. W. McLafferty (1993) "Interpretation of Mass Spectra" F. W. Benjamin, Inc, New York; D. C. Liebler (2002) "Introduction to Proteomics" Humana Press, New Jersey.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an oligonucleotide" includes a mixture of two or more oligonucleotides, and the like.

I. Definitions

In describing the present invention, the following terms will be employed, and are intended to be defined as indicated below.

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "loweralkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

The term "halo" or "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—SO₂—); phosphonyl (—PO₂—), and methine. Other carbonyl equivalents will be familiar to those having skill in organic chemistry.

The term "aryl" as used herein refers to cyclic aromatic hydrocarbon chains having twenty or fewer carbon atoms, e.g., phenyl, naphthyl, biphenyl and anthryl. One or more carbon atoms of the aryl group may also be substituted with, e.g.: alkyl; aryl; heterocycle; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, (x-methylbenzyl, phenethyl, and the like.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridinyl, phenazinyl, phenothiazinyl, phenoxazinyl, purinyl, benzimidazolyl, benzthiazolyl, and benzoxazolyl.

A "protein" or a "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation, ubiquitination, and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced. The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff =60; expect=10; Matrix=BLOSUM62; Descriptions=50 sequences; sort by=HICH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

As used herein, a "biological sample" refers to a sample of tissue or fluid isolated from a subject. Typical samples include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

As used herein, a "solid support" refers to a solid surface such as a magnetic bead, latex bead, microtiter plate well, glass plate, nylon, agarose, acrylamide, and the like.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

The present invention provides compositions and methods for use in the protein identification, protein sequencing, and identification of differential expression of proteins and peptides using mass spectrometeric techniques. The present method is practiced by labeling the N- or C-terminus of a protein or a peptide with the compositions of the present invention, fragmenting the labeled protein in the ionization zone of a mass spectrometer and determining the sequence. The labeled proteins and peptides are differentiated from unlabeled peptides by their unique mass signature in the resulting mass spectrum.

In one aspect, the present invention provides compositions for sequencing a protein or peptide, comprising a mass-tag label capable of reacting with any peptide generated in a proteolytic digest. The mass-tag label, referred to as "Universal Peptide Isotope Tag" (U-PIT) comprises a "reactive" group or functionality that is capable of reacting with an N-terminus or optionally a C-terminus of a peptide, an "isotopic-tag" group attached to the reactive group where the isotopic-tag group comprises light or heavy atoms, and a "charge replacement group" attached to the isotopic-tag group where the charge replacement group is capable of maintaining the overall charge of the protein or peptide that was present on the peptide before being labeled with the U-PIT reagent.

In another aspect, the present invention provides methods for identifying and/or sequencing a protein or a peptide, comprising:

(a) contacting a peptide with an N-terminus labeling moiety to covalently attach a label to the N-terminus of the peptide and form a tagged peptide, where the label is preferably U-PIT; and (b) analyzing the tagged peptide using a mass spectrometric fragmentation method to determine the sequence, identity and differential expression of the peptide.

Universal Peptide Isotope Tag Reagent (U-PIT)

In one aspect, the invention provides compositions useful in the sequencing, identification, and differential expression of proteins and peptides. The proteins or peptides in a sample are labeled with a tag, called "Universal Peptide Isotope Tag Reagent" (U-PIT). Often, the samples to be analyzed can comprise various perturbed states, such as, for example, healthy, diseased, or C-rich. Normally, the sample to be analyzed is divided into two parts, where one state of the sample is tagged with an isotopically labeled U-PIT and the sample from the other state is tagged with U-PIT that is not isotopically labeled.

U-PIT is designed such that it preferably reacts at least once, but preferably not more than once, with each peptide in the sample. The reagents of the invention can react with the N-terminus of the peptide, the C-terminus of the peptide, or the amino acid side chain of the C-terminus amino acid, such as, for example, lysine. However, the reagents preferably react with a primary amine or a tryptic cleavage site, such as arginine or lysine.

The U-PIT reagents for conducting methods in accordance with the present invention are protein class-specific reagents, or generic reagents, that comprise a reactive group capable of reacting with a nucleophilic site on the peptide, a moiety that is capable of being isotopically labeled, and a charge replacement group. The U-PIT reagents are generic in the sense that they can react with all or nearly all members of a particular class of proteins. Exemplary U-PIT reagents are shown in FIG. 1. In another aspect, the U-PIT reagents comprise another moiety that allows the separation of the U-PIT tagged peptides from the untagged peptides, if desired.

The U-PIT reagent can be additionally designed to maintain the charge state of the protein or the peptide. Thus, if the U-PIT reagent is designed to react with a primary amine on an protein or a peptide thereby removing a single positive charge, the reagent is designed such that it incorporates a single positive charge. Similarly, if U-PIT is designed to react with the C-terminus thereby removing a single negative charge, the reagent is negatively charged. Thus, the overall charge on the protein or peptide after tagging with U-PIT is the same as the charge for the untagged protein.

The U-PIT reagent can additionally be designed to incorporate a detectable label. The label for detection can be an enzyme, a radioactive isotope or a fluorophore. In addition, the U-PIT reagent can form bonds with the peptide that are stronger than the peptide bonds under the collisionally induced dissociation; it can be hydrophilic such that it does not affect the separation characteristics of the peptides; it can react with the target peptide rapidly at room temperature and in aqueous media and preferably yields the product quantitatively; it can be a chromophore or fluorophore thereby allowing for quantitation of the peptide; it can provide for ionizability for positive mode ESI-MS. In addition, the U-PIT reagent can be designed to be stable under shipping and storage conditions, forms a stable product with the target peptide, and can be non-toxic.

In one aspect of the invention, the U-PIT reagent comprises a reactive group (A), an isotopically tagged group (B) and a charge replacement group (C).

Nucleophilic Reactive Group (A)

In one aspect, the U-PIT reagent comprises a nucleophilic reactive group (A). The nucleophilic reactive group is capable of reacting with a nucleophile that may be present on the peptide. The nucleophile on the peptide may be N, S or O, such as a primary or secondary amine of an amino acid, or the carboxylate or phenolate of an amino acid of the peptide. The nucleophilic reactive group can thus normally be a leaving group that can be selected based on a particular nucleophilic group on the peptide chosen to be tagged.

When the nucleophile is an amine, the nucleophilic reactive group can include a reactive carbonyl or carbonyl equivalent, and a leaving group which may be displaced in a nucleophilic displacement reaction by the amine. "Carbonyl or carbonyl equivalent" includes, without limitation, carboxylic acids, esters, amides, anhydrides, acyl halides, and isocyantes. "Leaving group" means a moiety capable of nucleophilic displacement by an amine, e.g., $-NH_2$. Any leaving group can be used here provided it is readily removed by nucleophilic displacement. Non-limiting examples of leaving groups useful in the invention include halo, such as bromo, chloro, iodo, O-tosyl, O-triflyl, O-mesyl and the like. In addition, the leaving groups useful in the invention include succinimide, maleimide, glutarimide, isatin and phthalimide. The nucleophilic reactive group (A) preferably has a structure shown below:

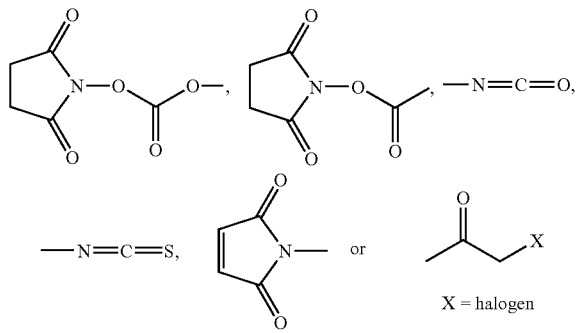

Isotopically Tagged Group (B)

The U-PIT reagent can additionally comprise a detectable moiety, such as, for example, a moiety capable of being isotopically labeled. The detectable moiety can be, for example, a label for detection by an enzyme, a radioactive isotope, a heavier isotope, or a fluorophore, preferably a heavier or lighter isotope. In one aspect, all the atoms in a selected region, comprising (B) or the detectable moiety, of the U-PIT reagent can be isotopically labeled. In another aspect, only one atom of B can be isotopically labeled, preferably between 2-15 atoms are isotopically labeled, more preferably between 2-9 atoms are isotopically labeled, and integers in between, such as, for example, 3, 4, 5, 6, 7, and 8. U-PIT is isotopically labeled such that the mass difference between the labeled and unlabeled regent is sufficiently high to allow for identification of the two forms of a doubly or triple charged peptide with a typical ion-trap resolution. However, the mass difference preferably is not so high that it causes differential retention effects for the peptides. Thus, the reagent preferably incorporates at least about 8 amu mass difference between the heavy and the light forms, preferably about 8 amu to about 100 amu mass difference, more preferably about 8 amu to about 50 amu mass difference, or most preferably about 8 amu to about 20 amu mass difference, or any integer between the stated ranges.

The preferred isotope can be selected from $^2H$, $^3H$, $^{13}C$, $^{14}C$, $^{32}P$, $^{34}S$, $^{35}S$, $^{36}Cl$, $^{37}Cl$, $^{18}O$, $^{15}N$, $^{81}Br$, $^{123}I$, $^{125}I$ and $^{131}I$, and combinations thereof.

In one aspect, the region of U-PIT that comprises the detectable moiety is an isotopically tagged group (B), and includes substituted 1,3,5-triazine having the structure below:

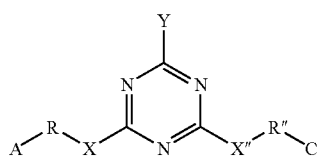

where A is the nucleophilic reactive group, C is the charge replacement group, Y can be H, $^2H$, $^3H$, $^{36}Cl$, or $^{37}Cl$, or of the formula: —X'—R'. In addition, X, and X" can be independently selected to be NH, O, or S, and R, and R" can be independently selected to be hydrogen, alkyl, alkenyl, alkynyl, aryl, heteroaryl, or $(CZ_2CZ_2O)_n$ where Z=H, $^2H$, $^3H$, and n is an integer between 1 and 15, preferably between 1 and 5. As will be evident to one of skill in the art, the natural atoms comprising the isotopically tagged group (B) of the U-PIT reagent can be replaced with varying numbers of $^2H$, $^{13}C$, $^{37}Cl$, or $^{15}N$, for example.

In another aspect of the invention, the isotopically tagged group of the U-PIT reagent comprises substituted or unsubstituted 1,2,4-triazine or 1,2,3-triazine, where the substituents are as described above. As will be evident to one of skill in the art, the triazine structure can be replaced with an aryl group, such as benzene, a heteroaryl group, such as pyridine, imidazole, pyrrole, or thiophene, or an alkyl group, such as ethyl, propyl, isoproyl, butyl, tert-butyl, polyethyleneglycol, and the like.

In another aspect, the isotopically tagged group additionally includes a detectable label such as a fluorophore, a radioactive isotope or an enzyme label. A number of fluorescent materials are known and can be utilized as labels. These include, for example, fluorescein, rhodamine, auramine, Texas Red, AMCA blue and Lucifer Yellow. Exemplary fluorescent dyes for use with the invention include water-soluble rhodamine dyes, fluoresceins, 4,7-dichlorofluoresceins, benzoxanthene dyes, and energy transfer dyes. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. Most preferably, the dye is a fluorescein or a fluorescein derivative.

The U-PIT reagent can also be labeled with a radioactive element or with an enzyme. The radioactive label can be detected by any of the currently available counting procedures. Enzyme labels are likewise useful, and can be detected by any of the presently utilized colorimetric, spectrophotometric, fluorospectrophotometric, amperometric or gasometric techniques. The enzyme can be conjugated to the U-PIT reagent by reaction with bridging molecules such as carbodiimides, diisocyanates, glutaraldehyde and the like. Many enzymes which can be used in these procedures are known. The preferred peroxidases are β-glucuronidase, β-D-glucosidase, β-D-galactosidase, urease, glucose oxidase plus peroxidase and alkaline phosphatase. In another aspect, the isotopic tagged group additionally includes an affinity label. The affinity label can be biotin, digoxin, fluorescein, dinitrophenol, and the like, that can bind to avidin, antibody for digoxin, antibody for fluorescein, and antibody for dinitrophenol, respectively.

Charge Replacement Group (C)

In one aspect of the invention, the U-PIT reagent comprises a charge replacement group (C). The charge replacement group can be selected based on ease of synthesis, increase in ionization efficiency of labeled peptides, and formation from a labeled peptide of a specific fragment ion series with minimal unfavorable label fragmentation. The charge replacement group includes compounds of the quaternary nitrogen derivatives, quaternary phosphonium derivatives, substituted pyridinium derivatives and sulfonium derivatives. Preferred charge replacement groups are dimethylalkylammonium derivatives and substituted or unsubstituted pyridinium derivatives.

The charge replacement components include, but are not limited to, primary, secondary, or tertiary alkyl or aryl ammonium groups, substituted and unsubstituted heterocyclyl and heteroaryl (e.g., pyridinium) groups, alkyl or aryl Schiff base or imine groups, and guanidino groups. In one aspect of the invention, the charge replacement moiety of the U-PIT reagent includes tetraalkyl or tetraaryl ammonium groups, tetraalkyl or tetraaryl phosphonium groups, and N-alkylated or N-acylated heterocyclyl and heteroaryl (e.g., pyridinium) groups. The quaternary nitrogen derivative can be $R_1R_2R_3N^+$—where $R_1$, $R_2$, and $R_3$ are independently selected to be H, lower alkyl, alkene, or aryl. For example, $R_1$, $R_2$, and $R_3$ can be H, methyl, propyl, isopropyl, butyl, tert-butyl, and the like.

The charge replacement group, as will be understood by one of ordinary skill in the art, will be accompanied by counterions of opposite charge. For example, the counterions for positively charged groups include oxyanions of lower alkyl organic acids (e.g., acetate), halogenated organic acids (e.g., trifluoroacetate), organosulfonates (e.g., N-morpholinoethane sulfonate), as well as $Cl^-$, $Br^-$, $HSO_4^-$, $BF_4^-$ and $ClO_4^-$.

Synthesis of U-PIT Reagents

The U-PIT reagents comprise the nucleophilic reactive group (A), the isotopically labeled group (B), and the charge replacement group (C), as described above. The compounds of the present invention, having the structure A-B-C, can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1H$ and $^{13}C$ NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts. U-PIT reagents represented by compounds in FIG. 1 can be synthesized using the following general procedures of Examples 1-4. The isotopically labeled U-PIT reagent can be prepared by either using isotopically labeled starting material or by making the unlabeled compounds and then isotopically labeling them by methods well known in the art.

Sample Preparation

In this aspect of the invention, the protein can be obtained from essentially any source. The protein can be isolated and purified to be free of interfering components. In one aspect of the invention, the protein is "substantially pure," which means that the protein is about 80% homogeneous, and preferably about 99% or greater homogeneous. Many methods well known to those of ordinary skill in the art may be utilized to purify the protein prior to its digestion or prior to determining its amino acid sequence. Representative examples include HPLC, Reverse Phase-High Pressure Liquid Chromatography (RP-HPLC), gel electrophoresis, chromatography, capillary electrophoresis, immobilized metal affinity chromatography (IMAC) or any of a number of peptide purification methods. The isolated protein can be contacted with a C-terminus or N-terminus labeling U-PIT reagent to covalently attach U-PIT reagent to the C- or N-terminus of the protein to form a tagged protein, suitable for analysis by mass spectrometric fragmentation methods.

Protein Digestion

In one aspect of the invention, the proteins are contained in a biological samples or may be recombinantly or synthetically produced. The proteins may be digested with any of the well-known protein digestion reagents. Such reagents may be chemical or enzymatic. Preferably, the N-termini of the peptide fragments obtained after digestion are free, i.e, the N-terminal end of each peptide is a free amino group. In this case, the free amino groups serve as a convenient location at which to label the peptides, as describe above.

The range of protein cleavage techniques include digestion by proteases including papain, clostropain, trypsin, LysC, GluC and by chemical digestion including limited acid digestion, and cyanogen bromide.

Proteases useful in practicing the present invention include without limitation trypsin, chymotrypsin, V8 protease, elastase, carboxypeptidase, papain, pepsin, proteinase K, thermolysin and subtilisin (all of which can be obtained from Sigma Chemical Co., St. Louis, Mo.). The protease for use in practicing the present invention is selected such that the protease is capable of digesting the particular target protein under the chosen incubation conditions. Papain cleaves on the carboxy-terminal side of Arg-X, Lys-X, His-X and Phe-X, and is a relatively mild protease, is commercially available in a highly purified form, and is available attached to solid supports (Sigma). The advantage of using a protease attached to a solid support is that this allows the complete and easy removal of the protease following digestion. Clostropain cleaves on the carboxy-terminal side of arginine residues, and is preferably used if the preferred cleavage site is Arg-Tyr. Trypsin is most commonly used for protein digestion, and cleaves on the carboxy-terminal side of arginine and lysine residues. However, if larger fragments are preferred, LysC can be used to digest the protein. LysC only cleaves at lysine residues, therefore, on average produces larger fragments than trypsin.

Typically, a target protein is first taken up to a final concentration of 2-100 μg/ml in a buffer. The buffer can be acetate, Tris, or phosphate buffer, at pH of about 5 to about 9, preferably pH of about 7 to about 8. The concentration of the buffer can be from about 1 nM to about 0.5 M, preferably about 10 mM to about 100 mM. The buffer can additionally contain other reagents such as, for example, calcium acetate and bovine serum albumin. The protease, such as trypsin, is then added to a final concentration of 2-10 µg/ml. Sequential or parallel incubations are then performed for different time periods ranging from 5 minutes to one hour, at temperatures ranging from 20° C. to 65° C. Reactions are terminated by addition of phenylmethylsulfonyl chloride (PMSF) to a final concentration of 1 mM and ethylenediaminotetraacetic acid (EDTA) to a final concentration of 20 mM. The amount of intact protein remaining in the reaction mixture at the end of the incubation period is then assessed by any of the following methods: polyacrylamide gel electrophoresis, ELISA, capillary electrophoresis (CE) or binding to nitrocellulose filters.

A chemical reagent for the protein digestion is cyanogen bromide (CNBr). As will be recognized by one skilled in the art, the conditions of the digest are adjusted such that peptides are produced which are amenable for separation, detection and identification.

The peptides may range in size from 1 amino acid to 50 or more, preferably about 5 amino acids to about 20 amino acids, depending on the protein sequence and the type of mass spectrometer to be used for analysis. Thus, the molecular weight for such peptides is from about 50 to 20,000 daltons. The molecular weight of the peptides for use in the invention is preferably about 200 amu to about 3000 amu, more preferably about 300 amu to about 1500 amu.

Tagging the Proteins and Peptides

The tagging of proteins with various U-PIT reagents described and disclosed above in an aqueous or mixed aqueous/organic solvent is known in the art and a wide range of labeling reagents and techniques useful in practicing the present invention are readily available to those of skill in the art. See, for example, Means et al. (1971) CHEMICAL MODIFICATION OF PROTEINS, Holden-Day, San Francisco. The tagged peptides can be purified using the methods known and described above.

In general, the peptide or the mixture of peptides is contacted with U-PIT reagent in an aqueous solvent. The solvent is preferably water, but can be a mixture of water and an organic solvent, such as, for example, DMSO, DMF, xylenes, acetone, and the like. The reaction mixture can contain a general acid-base catalyst in order to catalyze the reaction, such as, for example, tris buffer, phosphate buffer, acetate buffer, and the like. The reaction mixture can additionally contain coupling reagents such as dicyclohexylcarbodiimide, 2,3,5,6-tetrafluorophenyl trifluoroactate, 4-dimethylaminopyridine, transition metal-diamine complexes including Cu(II)phenanthroline, and enzyme for coupling the peptide with the U-PIT reagent.

Sequence and Identity Determination

The methods of the present invention are utilized in order to determine the sequence and/or identity of a protein. In one aspect of the invention, the tagging procedure is performed on a mixture of peptides. Following the tagging procedure the mixture of peptides is submitted to a separation process, which preferably, allows the separation of the protein mixture into discrete fractions.

In the methods of the present invention, the peptides tagged with the U-PIT reagents are sequenced by a mass spectrometer. Various mass spectrometers may be used within the present invention. Representative examples include, triple quadrupole mass spectrometers, magnetic sector instruments (magnetic tandem mass spectrometer, JEOL, Peabody, Mass.); ion-spray mass spectrometers; electrospray mass spectrometers; laser desorption time-of-flight mass spectrometers; quadrupole ion-trap spectrometers; and a Fourier Transform Ion Cyclotron Resonance Mass Spectrometer (Extrel Corp., Pittsburgh, Pa.). In one aspect of the invention, an electrospray mass spectrometer (Agilent Technologies, Palo Alto, Calif.) is utilized to fragment the tagged peptides, and a time-of-flight detector with better than 50 ppm mass accuracy is used to determine the sequence from the masses of the labeled fragments.

Although substantially pure peptides are preferably utilized within the methods described herein, it is also possible to determine the sequence of peptide mixtures. Briefly, in one aspect, an algorithm is utilized in order to determine all of the hypothetical sequences with a calculated mass equal to the observed mass of one of the peptides in the mixture (Johnson et al. (1992) Protein Science 1:1083-1091). These sequences are then assigned figures of merit according to how well each of them accounts for the fragment ions in the tandem mass spectrum of the peptide. Utilizing such algorithms, the sequence of polypeptides within the mixture may be readily determined.

One of skill in the art will appreciate that the sequence information obtained using the methods of the invention can be combined with other characteristics of the protein under analysis to even further reduce the number of possible identities of the protein. Thus, in a preferred embodiment, the method of the invention combines information from a protein sequence tag with one or more other protein characteristics to identify the protein. Data that are useful to supplement the sequence data include, but are not limited to, amino acid composition, the number and identity of specific residues (e.g. cysteine), cleavage information, proteolytic (e.g., tryptic) and or chemolytic peptide mass, subcellular location, and separation coordinates (e.g., retention time, pI, 2-D electrophoresis coordinates, etc.). Other forms of data characteristic of a particular protein or class of proteins that can be combined with information from use of the compositions and methods of the invention to identify a protein will be apparent to those of skill in the art. As the body of data characteristic of a particular protein becomes more comprehensive, proteins under analysis can be identified using shorter sequences.

Differential Expression

In one aspect of the invention, the U-PIT compounds are used in methods for detecting the differential expression of the same protein in two samples, or the presence of protein(s) in some, but not all, samples. The present invention thus provides methods of identifying one protein or more than one protein, that are differentially present in samples. The samples, as defined above, include, for example, sample from a healthy patient and a samples from a diseased patient. When the samples are biological specimen, the information provided by the inventive methods may be used to determine which protein(s) are differentially expressed in the samples. As used herein, the term "differentially present" means that one or more proteins is present at a higher relative amount in one of the samples as compared to the rest of the samples. The term also means that protein(s) are present in one of the samples that are not present in the rest of the samples.

In one aspect of the present invention, peptides from two or more samples are analyzed separately, or the peptide mixtures can be combined for analyses in a single analytical run. The peptide mixtures can be obtained from different sources and the peptides are then differentially labeled. The use of differential labeling for the two samples yields one sample peptide mixture with a characteristic label, such as, for example, a U-PIT tag of the invention, whereas the peptides in the other sample mixture bear a different characteristic label, such as, for example isotopically labeled U-PIT tag. Once the mixtures are combined and then subjected to analysis by mass spectrometric means described above, variations in the ratio of signals from the two labels indicates different amounts of that particular peptide, and, thus, differential expression of the precursor protein.

The compositions and methods of the invention are thus useful for identifying proteins from a healthy or a diseased tissue sample. In one aspect, the compositions and methods are applied to both a mixture of proteins from a healthy tissue sample and a mixture of proteins from a diseased tissue sample. The samples can then be analyzed individually or as a mixture, as described above.

In another aspect of the invention, the compositions and methods of the invention are applied to a plurality of samples where each sample can contain a single protein or a mixture of proteins. In this aspect of the invention, each sample is labeled with a selected U-PIT reagent of the invention which differs from the U-PIT reagent used for all other samples by at least 1 mass units. The difference in mass is preferably achieved by differentially isotopically labeling the U-PIT reagent. The differential isotopic labeling can be achieved by varying the isotopically tagged group (B) by the desired mass units. The compositions and methods of the invention thus find use in proteomics.

Phosphopeptides

One post-translational modification of proteins is the addition or removal of phosphate groups. Protein phosphorylation and de-phosphorylation reactions have been established as major components of metabolic regulation and signal transduction pathways. Variations in protein phosphorylation provide the predominant means of enzymatic regulation now known in biological systems, especially in the regulation of signal transduction from cell surface receptors. Reversible phosphorylation is important for transmitting regulatory signals, including proliferative ones, in all living cells. To understand the molecular basis of these regulatory mechanisms, it is necessary to identify the specific amino acid residues that become phosphorylated. By identifying the substrates and sites of phosphorylation, diagnostic tools may be developed for some tumors and the modification of the process itself could be a target for therapeutic intervention.

Polypeptides such as growth factors, differentiation factors and hormones, are crucial components of the regulatory system that coordinates development of multicellular organisms. Many of these factors mediate their pleiotropic actions by binding to and activating cell surface receptors with an intrinsic protein tyrosine kinase activity. Changes in cell behavior induced by extracellular signaling molecules such as growth factors and cytokines require execution of a complex program of transcriptional events. To activate or repress transcription, transcription factors must be located in the nucleus, bind DNA, and interact with the basal transcription apparatus. Accordingly, extracellular signals that regulate transcription factor activity may affect one or more of these processes. Most commonly, regulation is achieved by reversible phosphorylation. Phosphorylation of a transcription factor by several different kinases (or by a kinase linked to more than one pathway) is a simple mechanism that allows different signals to converge at the same factor.

There are a number of approaches in the literature directed to the analysis of phosphorylation. One such method is two-dimensional phosphopeptide mapping of $^{32}$P-labeled proteins. Another approach relies on mass spectrometry for analysis of non-radiolabeled phosphoproteins. In another approach (Cao, et al, Rapid Commun. Mass Spectrom. (2000) 14:1600-1606) phosphorylation sites of proteins are mapped using on-line immobilized metal affinity chromatography (IMAC)/capillary electrophoresis (CE)/electrospray ionization multiple stage tandem mass spectrometry (MS). The IMAC resin retains phosphorylated proteins and peptides, CE separates the phosphopeptides of a mixture eluted from the IMAC resin, and MS provides information including the phosphorylation sites of each component.

A procedure for micropurification of phosphorylated peptides, as a front end to mass spectrometric analysis, is disclosed by Posewitz, et al., Anal. Chem. (1999) 71: 2883-2892. Immobilized metal affinity chromatography in a microtip format and more specifically, in combination with gallium III ions is employed. Phosphopeptides are retrieved in near quantitative and highly selective manner, to yield a concentrated sample for direct analysis by matrix-assisted laser desorption/ionization time of flight and nanoelectrospray ionization mass spectrometry.

In one aspect of the invention, the U-PIT tagged peptides are purified using IMAC or by affinity chromatography based on either natural antibodies or synthetic antibody mimics. Typically, each biological sample containing phosphopeptides can be denatured, reduced and alkylated, and then subjected to tryptic digestion. The peptides thus obtained can be divided into two samples. One peptide sample can be tagged with the unlabeled U-PIT reagent while the other peptide sample can be tagged with the isotopically labeled U-PIT reagent. The two peptide samples can then be combined, the phosphopeptides separated by affinity or IMAC based separation methods, and the sequence and relative amounts determined as described below.

In another aspect, the biological sample can be reduced, alkylated and subjected to tryptic digestion. The sample is then purified by IMAC or affinity chromatography to capture the phosphorylated peptides, and the captured phosphorylated peptides are tagged with isotopically labeled U-PIT reagent. The non-phosphorylated peptides, separated above, can then be phosphorylated in vitro by enzymatic phosphorylating-susceptible peptides. The in vitro phosphorylated peptides can be purified by IMAC or affinity chromatography to capture the phosphorylated peptides, and tagged with non-isotopically labeled U-PIT reagent. The two samples can then be pooled and analyzed as described below.

The present invention thus provides for isotopically tagging peptides that are decoupled from the affinity-based selection of the peptides. Thus, tagging and selection of the peptides can be independently optimized.

Kits

The subject sets of U-PIT reagents may be sold in kits, where the kits may or may not comprise instructions for use, and additional reagents or components necessary for the particular application in which the U-PIT reagent is to be employed. Thus, for sequencing applications, the sets may be sold in a kit which further comprises one or more of the additional requisite sequencing reagents, such as peptide digestion enzymes, polymerases, nucleotides, buffers, separation columns for particular peptides or proteins, such as affinity columns or IMAC columns, software, and the like.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Synthesis of 2-Ethylamino-4,6-Dichloro-s-Triazine (2)

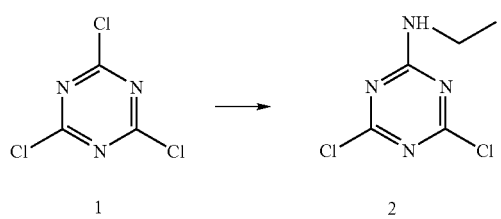

2,4,6-Trichloro-s-triazine (1, 1 g, 5.4 mmol), and ethylamine hydrochloride (0.44 g, 5.4 mmol) were combined in a round bottom flask and cooled to −5° C. using an ice-salt bath. To the cooled, stirred solution was added N,N-diisopropylethylamine (1.88 mL, 10.8 mmol). The resultant yellow colored solution was stirred at −5° C. for 1 h, the solvents removed under reduced pressure, and the resultant residue was dissolved in 1:1 v/v of ethyl acetate and water. The organic layer was separated, washed with saturated solution of $NaHCO_3$, and dried over $Na_2SO_4$. The organic solvent was removed under reduced pressure to yield an orange colored solid. The solid was triturated with hexane to yield the product 2 as a yellow-orange powder (0.7 g) with a yield of 68%.

EXAMPLE 2

Synthesis of Substituted Triazine (3)

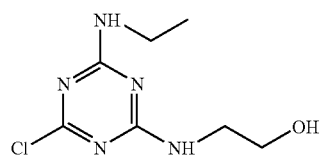

2-Ethylamino-4,6-dichloro-s-triazine (2, 0.36 g, 1.88 mmol) prepared in Example 1 and ethanolamine hydrochloride (0.18 g, 1.88 mmol) were dissolved in 15 mL of absolute ethanol, and then N,N-diisopropylethylamine (0.65 mL, 3.76 mmol) was added. The solution was heated under reflux for about 20 h. The reaction solution was cooled to room temperate, the volatile components removed under reduced pressure, and the resultant residue was dissolved in 1:1 v/v of ethyl acetate and water. The organic layer was separated, washed with saturated solution of $NaHCO_3$, and dried over $Na_2SO_4$. The organic solvent was removed under reduced pressure to yield a pale yellow colored powder in a 41% yield.

The yellow colored powder was further purified by LC-MS using a preparative Zorbax SB-C18 column (9.4 mm×25 cm) with a flow rate of 4 mL/min. Solvent A was 0.1% trifluoroacetic acid (TFA) in water. Solvent B was 0.1% TFA in acetonitrile. A linear gradient was used for the initial 2 min. until 10% solvent B was reached. Solvent B was increased to 18% over the next 16 min., increased to 100% solvent B over a 1 min. interval, and the column was flushed with 100% solvent B for the next 6 min. The product 3 was collected in the 13-15 min. time interval as a white crystalline solid. ES-MS, m/z=218 [M+H]$^+$ and the isotope pattern consistent with 1 chlorine atom present was observed.

EXAMPLE 3

Synthesis of Substituted Triazine (4)

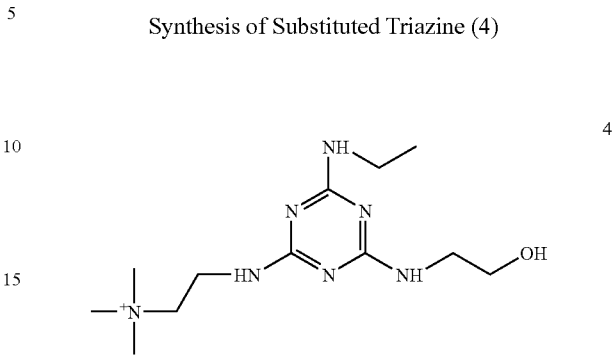

Compound 3 (30 mg, 0.276 mmol) synthesized and purified in Example 2 was dissolved in 10 mL of dry n-propanol, and then (2-aminoethyl)trimethylammonium chloride (50 mg, 0.276 mmol) and N,N-diisopropylethylamine (50 µL, 0.276 mmol) were added. The solution was heated under reflux for 2.5 days. The volatile components were removed under reduced pressure, and the residue was placed under high vacuum for several hours, usually 5-8 h. The residue thus obtained was dissolved in the minimal amount of water, and the solution was passed through a Bakerbond™ spe Octadecyl (C18) disposable extraction cartridge (J. T. Baker, Phillipsburg, N.J.) containing 1 g of media. The cartridge was initially washed with water to remove salts and base, and the product was subsequently flushed from the column with 50%-100% acetonitrile/water solvent mixtures. The collected solvents were evaporated to yield 60 mg of 4 as a white crystalline film (75% yield). The product was identified by its fragmentation pattern in ES-MS, m/z=284 [M$^+$].

EXAMPLE 4

Synthesis of Substituted Triazine (5)

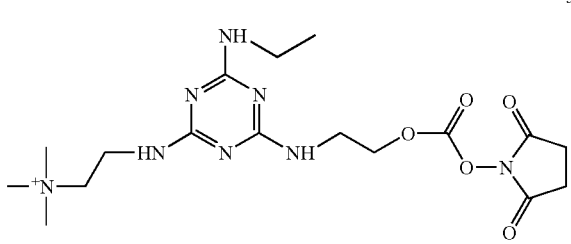

Compound 4 prepared in Example 3 was dissolved in 5 mL of dry dioxane. Separately, a suspension was prepared by placing N,N'-disuccinimidyl carbonate (DSC, 0.31 g, 1.2 mmol) in 8 mL of dry acetone. The suspension was added to the dioxane solution, followed by the addition of N,N-diisopropylethylamine (210 µL, 0.2 mmol). After approximately 20 min., a clear solution begins to form. The solution was stirred under a nitrogen atmosphere for 20 h at room temperature. The volatile components were removed under reduced pressure, and the residue was placed under high vacuum for several hours, usually 5-8 h. The residue thus obtained was highly water soluble.

The residue was purified on a LC-MS using polyhydroxyethyl A (4.6 mm×10 cm, 5 μm/20 nm pore), a hydrophobic interaction column obtained from PolyLC, Inc. (Columbia, Md.). Solvent A was 10 mM ammonium formate. Solvent B was 10 mM ammonium formate in acetonitrile:water (9:1 v/v). A linear gradient was used to decrease the initial 100% solvent B to 50% solvent B in 15 min. Then solvent A was increased to 100% over 1 min, and the column flushed with solvent A for an additional minute. The desired product 5 was collected in the 7.5-8 min. time interval as a white crystalline solid. ES-MS, m/z=310 [M-hydroxysuccinimate]$^+$.

EXAMPLE 5

Tagging Peptides with Compound (5)

Figure 2:
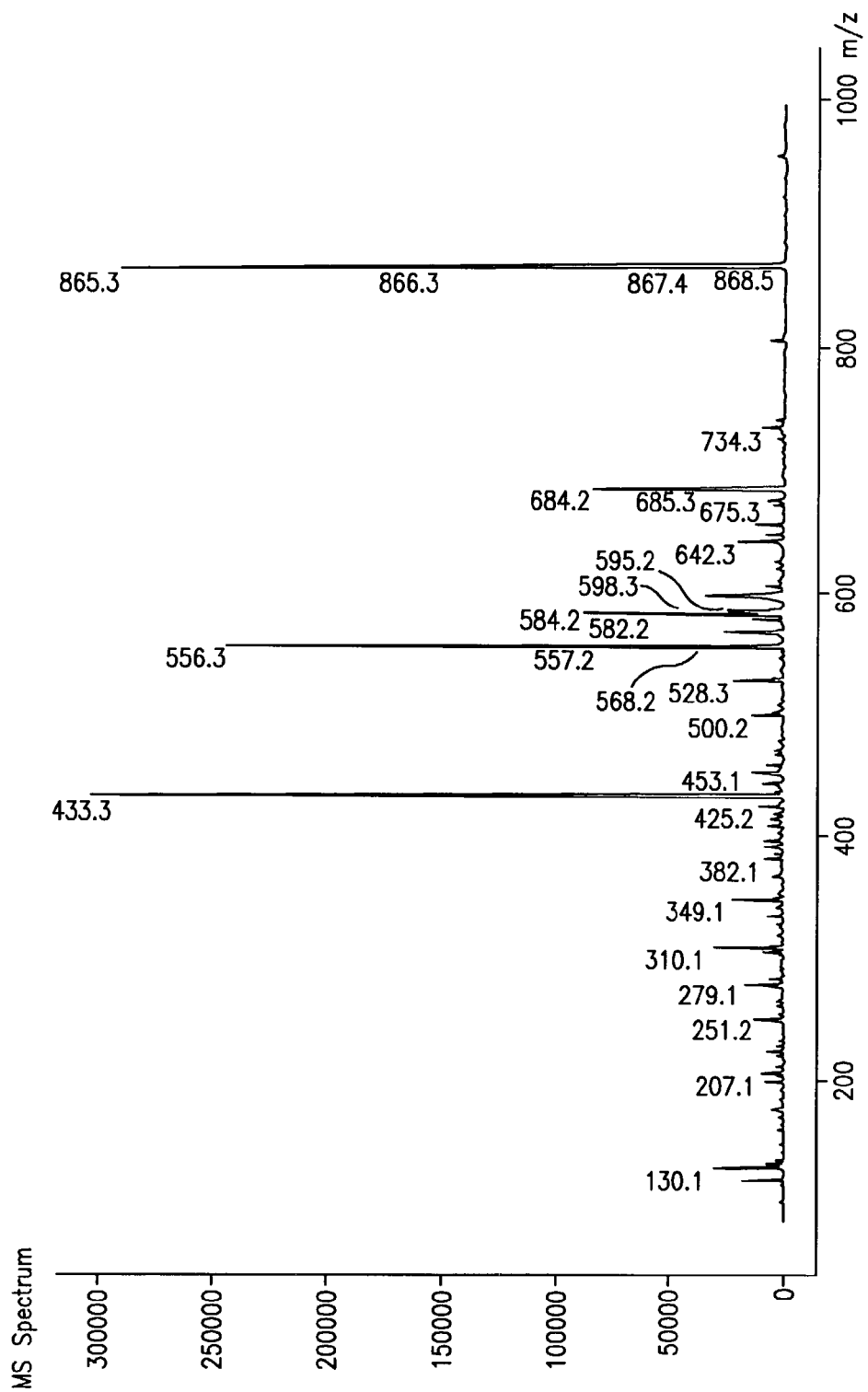
FIG. 2 depicts the mass spectra of U-PIT-tagged leucine enkephalin.

Compound 5 (3 mg, 7 μmol) prepared in Example 4 was dissolved in 200 μL of pH 7.8 100 mM phosphate buffer. Leucine enkephalin (1 μg, 1.4 μmol) was dissolved in 50 μL of the pH 7.8 phosphate buffer, and then added to the solution of compound 5. The colorless solution was gently shaken overnight at 30° C. The solution was then passed through a pasteur pipette filled with C18 media up to the 2 cm mark to remove the phosphate salts in the reaction solution, and then washed with methanol. The methanol was collected and analyzed with ES-MS. The m/z=865 [M]$^+$ is consistent with the presence of tagged-leucine enkephalin (FIG. 2).

EXAMPLE 6

Tagging Peptides with Compound (6)

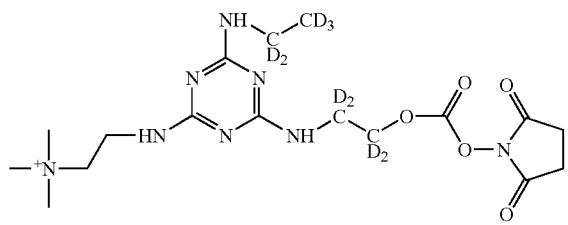

Figure 3:
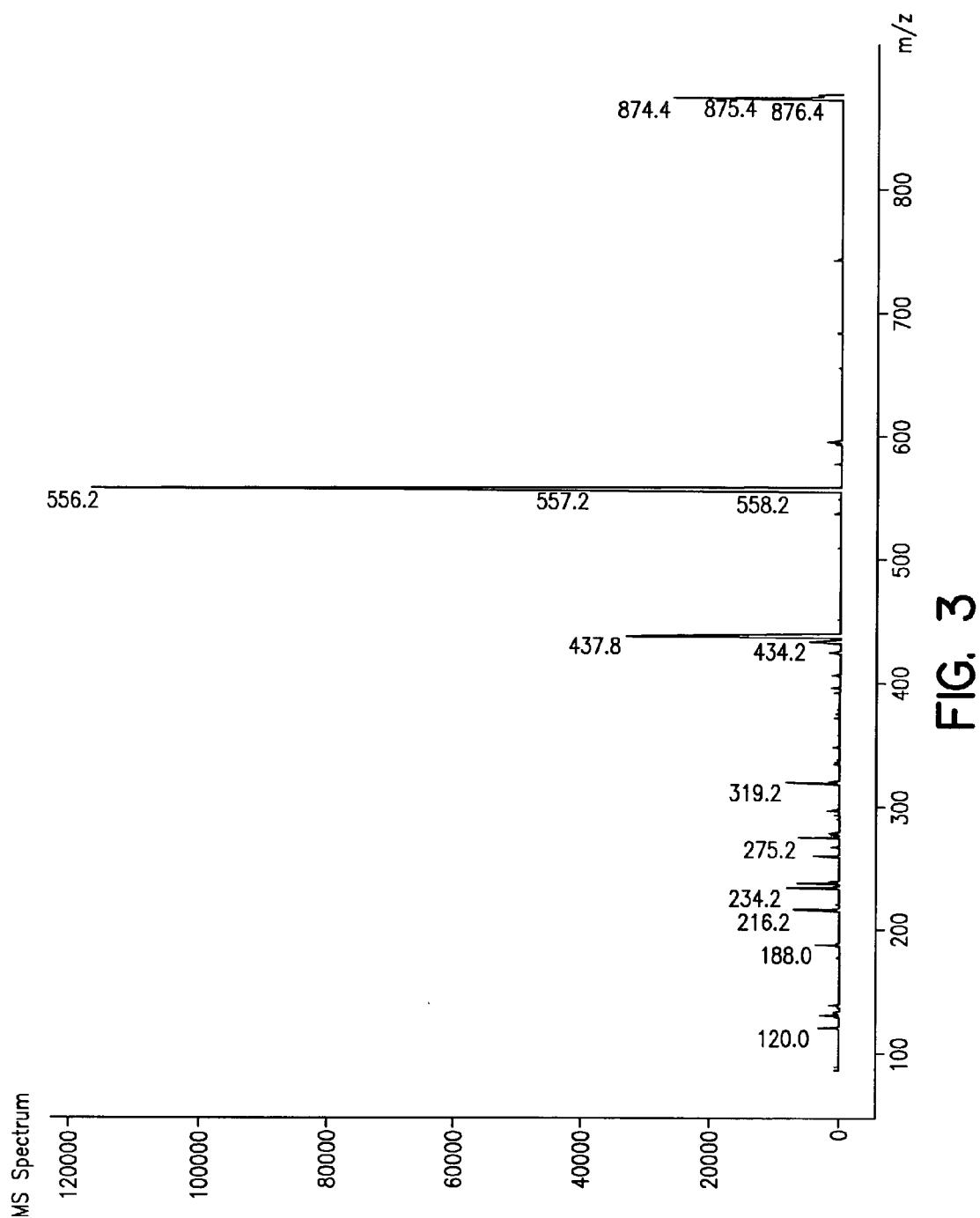
FIG. 3 depicts the mass spectra of U-PIT-tagged leucine enkephalin where the U-PIT reagent is isotopically labeled.

Compound 6 was prepared as described in Examples 1-4, except ethyl-d$_5$-amine and ethanol-1,1,2,2-d$_4$-amine were used. Leucine enkephalin was tagged with the isotopically labeled compound 6 according to Example 5, and analyzed with ES-MS. The m/z=874 [M]$^+$ is consistent with the presence of isotopically tagged-leucine enkephalin (FIG. 3).

EXAMPLE 7

Analysis of Mixed Samples

Figure 4:
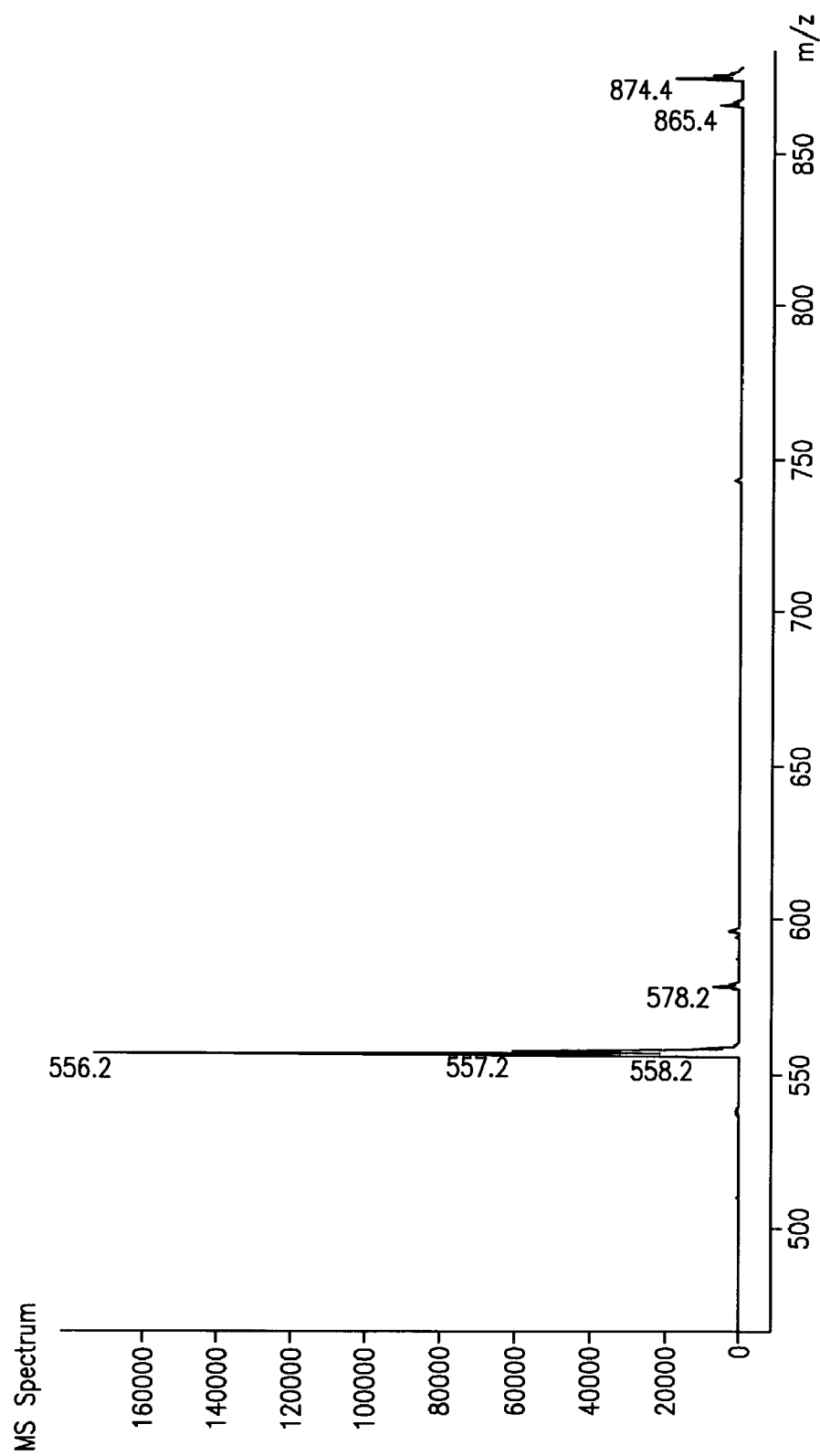
FIG. 4 depicts the mass spectra of U-PIT-tagged leucine enkephalin, where the ratio of the unlabeled to labeled tag is 1:3.

Solutions containing leucine enkephalin tagged with the isotopically labeled compound 6 and non-isotopically labeled compound 5 were combined in a 3:1 ratio (labeled: unlabeled, v/v). The combined solution was then analyzed with ES-MS. The m/z=874 [M]$^+$ and m/z=865 [M]$^+$ are consistent with the presence of labeled and unlabeled tagged-leucine enkephalin (FIG. 4).

Accordingly, novel compounds and the use of the compounds for identifying, sequencing, and examining the differential expression of proteins and peptides have been disclosed. From the foregoing, it will be appreciated that, although specific embodiments of the invention have been described herein for purposes of illustration, various modifications may be made without deviating from the spirit and scope thereof.

We claim:

1. A compound of formula:

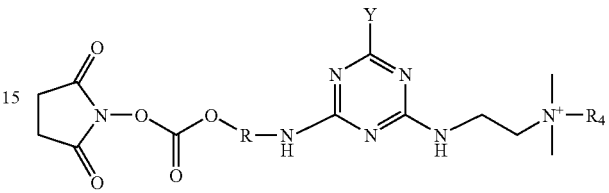

where R is selected from the group consisting of alkyl, alkenyl, alkynyl, aryl, heteroaryl, and (CH$_2$CH$_2$O)$_n$ where n is an integer between 1 and 5;

R$_4$ is selected from the group consisting of hydrogen, lower alkyl and aryl; and Y is H, halogen or of the formula:

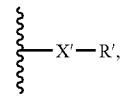

where X' is NH, O, or S; and

R' is selected from the group consisting hydrogen, alkyl, alkenyl, alkynyl, aryl, and heteroaryl.

2. The compound of claim 1, wherein X' is NH, and R$_4$ is methyl or tert-butyl.

3. The compound of claim 2, wherein R' is ethyl.

4. The compound of claim 2, wherein R is CH$_2$CH$_2$ or CH$_2$CH$_2$OCH$_2$CH$_2$.

5. The compound of claim 2, wherein X', R' and R are isotopically labeled.

6. The compound of claim 5, wherein R' is C$^2$H$_2$C$^2$H$_3$ and R is C$^2$H$_2$C$^2$H$_2$, CH$_2$CH$_2$OC$^2$H$_2$C$^2$H$_2$, or C$^2$H$_2$C$^2$H$_2$OC$^2$H$_2$C$^2$H$_2$.

7. A compound of formula:

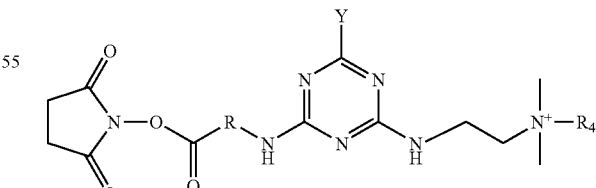

where R is selected from the group consisting of alkyl, alkenyl, alkynyl, aryl, heteroaryl, and (CH$_2$CH$_2$O)$_n$ where n is an integer between 1 and 5;

R$_4$ is selected from the group consisting of hydrogen, lower alkyl and aryl and Y is H, halogen or of the formula:

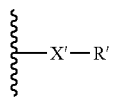

where X' is NH, O, or S; and
R' is selected from the group consisting hydrogen, alkyl, alkenyl, alkynyl, aryl, and heteroaryl.

8. The compound of claim 7, wherein X' is NH, and $R_4$ is methyl or tert-butyl.

9. The compound of claim 7, wherein X', R' and R are isotopically labeled.

10. The compound of claim 8, wherein R' is ethyl.

11. The compound of claim 10, wherein R is $CH_2CH_2$ or $CH_2CH_2OCH_2CH_2$.

12. The compound of claim 9, wherein R' is $C^2H_2C^2H_3$ and R is $C^2H_2C^2H_2$, $CH_2CH_2OC^2H_2C^2H_2$, or $C^2H_2C^2H_2OC^2H_2C^2H_2$.

13. A compound or formula:

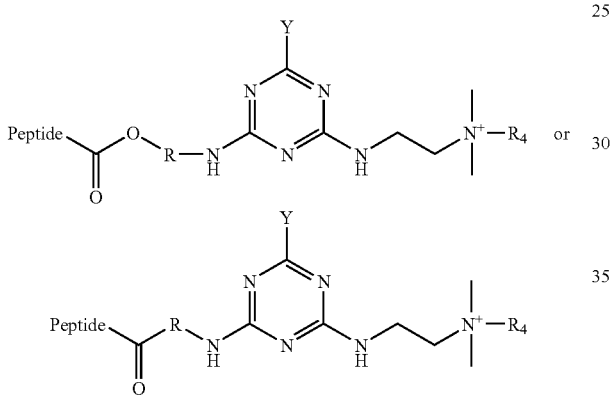

where R is selected from the group consisting of alkyl, alkenyl, alkynyl, aryl, heteroaryl, and $(CH_2CH_2O)_n$ where n is an integer between 1 and 5;
$R_4$ is selected from the group consisting of hydrogen, lower alkyl and aryl, and
Y is H, halogen or of the formula:

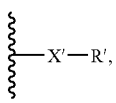

where X' is NH, O, or S; and
R' is selected from the group consisting hydrogen, alkyl, alkenyl, alkynyl, aryl, and heteroaryl.

14. The compound of claim 13, wherein X' is NH, and $R_4$ is methyl or tert-butyl.

15. The compound of claim 13, herein X', R' and R are isotopically labeled.

16. The compound of claim 13, wherein the peptide comprises a phosphoryl group.

17. The compound of claim 14, wherein R' is ethyl.

18. The compound of claim 14, wherein R is $CH_2CH_2$ or $CH_2CH_2OCH_2CH_2$.

19. The compound of claim 15, wherein R' is $C^2H_2C^2H_3$ and R is $C^2H_2C^2H_2$, $CH_2CH_2OC^2H_2C^2H_2$, or $C^2H_2C^2H_2OC^2H_2C^2H_2$.

20. A kit for detecting the presence of a plurality of target peptides in a sample, the kit comprising a compound of formula:

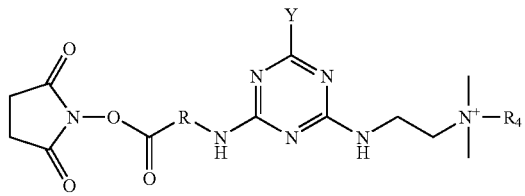

where
R is selected from the group consisting of, alkyl, alkenyl, alkynyl, aryl, and heteroaryl;
$R_4$ is selected from the group consisting of hydrogen, lower alkyl and aryl; and
Y is H, halogen or of the formula:

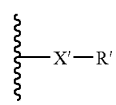

where X' is NH, O, or S; and
R' is selected from the group consisting of, alkyl, alkenyl, alkynyl, aryl, and heteroaryl; and
written instructions.

21. A kit for detecting the presence of a plurality of target peptides in a sample, the kit comprising a compound of formula:

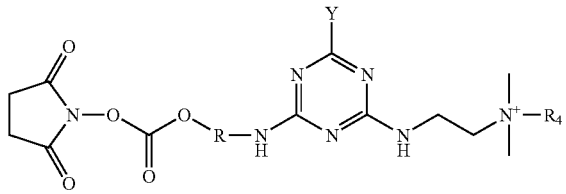

where R is selected from the group consisting of alkyl, alkenyl, alkynyl, aryl, heteroaryl, and $(CH_2CH_2O)_n$ where n is an integer between 1 and 5;
$R_4$ is selected from the group consisting of hydrogen, lower alkyl and aryl; and
Y is H, halogen or of the formula:

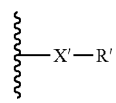

where X' is NH, O, or S; and
R' is selected from the group consisting hydrogen, alkyl, alkenyl, alkynyl, aryl, and heteroaryl; and
written instructions.

22. The kit of claim 20, further comprising means for separating a class of peptides.

23. The kit of claim 20, further comprising buffers and protein digestion enzymes.

24. The kit of claim 21, further comprising means for separating a class of peptides.

25. The kit of claim 21, further comprising buffers and protein digestion enzymes.

26. The kit of claim 22, wherein the means for separating comprises an affinity column.

27. The kit of claim 24, wherein the means for separating comprises an affinity column.

* * * * *

UNITED STATES PATENT AND TRADEMARK OFFICE
CERTIFICATE OF CORRECTION

| | |
|---|---|
| PATENT NO. | : 7,425,451 B2 |
| APPLICATION NO. | : 10/318845 |
| DATED | : September 16, 2008 |
| INVENTOR(S) | : Robotti et al. |

It is certified that error appears in the above-identified patent and that said Letters Patent is hereby corrected as shown below:

In column 21, line 61, in Claim 15, delete "herein" and insert -- wherein --, therefor.

In column 22, line 19, in Claim 20, delete "of," and insert -- of --, therefor.

In column 22, line 32, in Claim 20, delete "of," and insert -- of --, therefor.

Signed and Sealed this

Sixth Day of January, 2009

JON W. DUDAS
*Director of the United States Patent and Trademark Office*